US006338847B1

(12) United States Patent
Thomas

(10) Patent No.: US 6,338,847 B1
(45) Date of Patent: Jan. 15, 2002

(54) COMPOSITIONS AND METHODS TO DISINFECT CONTACT LENSES

(75) Inventor: Larry K. Thomas, Fullerton, CA (US)

(73) Assignee: Allergan, Waco, TX (US)

( * ) Notice: Subject to any disclaimer, the term of this patent is extended or adjusted under 35 U.S.C. 154(b) by 0 days.

(21) Appl. No.: 08/203,837

(22) Filed: Feb. 28, 1994

Related U.S. Application Data

(63) Continuation of application No. 08/009,907, filed on Jan. 26, 1993, now abandoned.

(51) Int. Cl.[7] ............................................... A61K 38/54
(52) U.S. Cl. .................... 424/94.2; 424/94.4; 424/94.6; 424/94.61; 424/94.62; 424/94.63; 424/94.64; 424/94.65; 424/94.66; 424/94.67; 422/30; 252/95; 252/106; 252/174.12; 252/174.13
(58) Field of Search ............................... 424/94.2, 94.4, 424/94.6, 94.61, 94.62, 94.63, 94.64, 94.65, 94.66, 94.67; 422/30; 252/95, 106, 174.12, 174.13

(56) References Cited

U.S. PATENT DOCUMENTS

| 3,910,296 A | 10/1975 | Karageozian et al. | 134/2 |
|---|---|---|---|
| 3,912,451 A | 10/1975 | Gaglia, Jr. | 422/30 |
| 4,521,375 A | 6/1985 | Houlsby | 422/29 |
| 4,557,925 A | 12/1985 | Lindahl et al. | 424/482 |
| 4,568,517 A | 2/1986 | Kaspar et al. | 422/30 |
| 4,588,586 A | 5/1986 | Kessler et al. | 424/94.4 |
| 4,670,178 A | 6/1987 | Huth et al. | 422/28 |
| RE32,672 E | 5/1988 | Huth et al. | 435/264 |
| 4,749,511 A | 6/1988 | Lad et al. | 510/114 |
| 4,767,559 A | 8/1988 | Kruse et al. | 510/114 |
| 4,775,424 A | 10/1988 | Wisotzki et al. | 134/42 |
| 4,880,601 A | 11/1989 | Andermann et al. | 422/28 |

FOREIGN PATENT DOCUMENTS

| DE | 3626082 | 2/1988 |
|---|---|---|
| EP | 0082798 | 6/1983 |
| EP | 0147100 | 7/1985 |
| EP | 0209071 | 1/1987 |
| EP | 02 55041 A1 | 3/1988 |
| EP | 0278224 | 8/1988 |
| GB | 2139260 A | 11/1984 |
| GB | 2151039 A | 7/1985 |
| GB | 2173017 A | 10/1986 |
| WO | WO8605693 | 10/1986 |
| WO | WO0901178 | 10/1990 |
| WO | WO9117469 | 11/1991 |

OTHER PUBLICATIONS

Eudragit L, Data Sheet (L 12,5, Info L–2/e).
Chemical Abstracts Selects: Controlled Release Technology Issue 2, 1987, p. 4, 106:9424f.
Abstract 92061537A,The efficacy of disinfection system using hydrogen peroxide against acanthamoeba. Izumi Y et al. J. Jpn Contact Lens Soc 1991:33(4):282–6.

*Primary Examiner*—Jean C. Witz
(74) *Attorney, Agent, or Firm*—Stout, Uxa, Buyan & Mullins, LLP

(57) ABSTRACT

Compositions and methods to disinfect contact lenses are disclosed. In one embodiment, the present composition comprises a cellulose decomposing enzyme component, e.g., lysozyme, and a hydrogen peroxide destroying component. The composition is structured so that the cellulose decomposing enzyme component is released in a liquid medium containing hydrogen peroxide before the hydrogen peroxide destroying component is released in the liquid medium. Such cellulose decomposing enzyme component is preferably effective to render hydrogen peroxide-resistant microorganisms, e.g., acanthamoeba cysts, which may contaminate the lens more susceptible to being killed by hydrogen peroxide.

15 Claims, No Drawings

COMPOSITIONS AND METHODS TO DISINFECT CONTACT LENSES

This application is a continuation of application Ser. No. 08/009,907, filed Jan. 26, 1993 now abandoned.

BACKGROUND OF THE INVENTION

This invention relates to compositions and methods to disinfect contact lenses. More particularly, the invention relates to such compositions and methods which are useful to facilitate the action of hydrogen peroxide in disinfecting contact lenses and in destroying residual hydrogen peroxide present in a liquid aqueous medium containing a contact lens which has been disinfected by the action of hydrogen peroxide.

Contact lenses should be periodically cleaned and disinfected by the user to prevent infection or other deleterious effects on ocular health which may be associated with contact lens wear. Currently, there are several different conventional systems and methods which enable the user to clean and disinfect their contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are hydrogen peroxide disinfection systems. Disinfecting hydrogen peroxide solutions are effective to kill many of the bacteria, fungi and yeasts which may contaminate contact lenses. However, certain microorganisms are resistant to the action of hydrogen peroxide.

One microorganism which is resistant to the killing effects of hydrogen peroxide is the cyst form of acanthamoeba. It has been reported, in an article entitled "The Efficacy of Disinfection System Using Hydrogen Peroxide Against Acanthamoeba", by Y. Izumi et al, J. Japanese Contact Lens Society 1991; 33(4): 282–6, that such cysts exposed to hydrogen peroxide for two hours survived after two weeks. This article discloses that inclusion of lysozyme in the hydrogen peroxide solution resulted in killing all the cysts within 30 minutes. This article does not suggest any specific contact lens disinfecting system to take advantage of this observation. Since lysozyme is a primary tear protein, the purposeful addition of this enzyme to a liquid medium containing a contact lens may disadvantageously result in the formation of proteinaceous deposits on the contact lens. In effect, treatment of a contact lens with a hydrogen peroxide solution containing lysozyme may result in the lens being soiled with proteinaceous deposit material and/or being otherwise detrimentally affected. In addition, disinfecting a contact lens with a hydrogen peroxide solution containing lysozyme does nothing to destroy the potentially harmful residual hydrogen peroxide which remains after the lens is disinfected.

Residual hydrogen peroxide on a disinfected contact lens may cause irritation, burning or trauma to the eye unless this hydrogen peroxide is destroyed, i.e., decomposed, neutralized, inactivated or chemically reduced. Therefore, the destruction of the residual hydrogen peroxide in the liquid medium containing the disinfected contact lens is needed to enable safe and comfortable wear of the disinfected contact lens.

Associated with the problem of hydrogen peroxide destruction in contact lens disinfection systems are the problems of easy use and user compliance. To enhance user compliance and ease of use, several efforts have focused on one-step disinfection and hydrogen peroxide destruction. In this regard, various time release tablets containing a core tablet and a coating have been suggested. Kruse et al U.S. Pat. No. 4,767,559 discloses a one-step contact lens cleaning and disinfecting tablet designed to be totally dissolved in water. A core containing a hydrogen peroxide reducing agent and a catalyst is provided. A jacket mixture containing a hydrogen peroxide generating component is provided and envelopes the core. In this case, the jacket mixture dissolves to form hydrogen peroxide to disinfect the contact lens. Subsequently, a thin lacquer coating surrounding the core of the tablet is dissolved, resulting in the release of the reducing agent and catalyst.

Kay United Kingdom Patent Application GB 2 151 039 A discloses a sustained-release tablet composition from which a hydrogen peroxide inactivator, e.g. sodium sulphite, is gradually leached in the presence of a hydrogen peroxide-containing solution used to disinfect contact lenses. The entire tablet, other than the leached hydrogen peroxide inactivator, remains unaffected, i.e., is insoluble in the solution.

Kaspar et al U.S. Pat. No. 4,568,517 discloses a system in which a contact lens is disinfected in an aqueous hydrogen peroxide solution and, after disinfection, the peroxide is reduced by adding a tablet containing a core having a hydrogen peroxide reducing component, e.g. sodium sulfite or sodium thiosulfate, and a coating which slowly totally dissolves in the peroxide solution to release the reducing agent.

A number of other alternatives for a combination tablet or the like containing a hydrogen peroxide sterilizing agent and a hydrogen peroxide reducing agent are disclosed in Schafer et al European Patent Application 86-109,361.5. None of these patents and patent applications disclose the use of components which facilitate the antimicrobial action of hydrogen peroxide.

Accordingly, a need exists for novel, safe and efficacious systems for killing hydrogen peroxide-resistant microorganisms contaminating contact lenses without detrimentally affecting, e.g., soiling and/or otherwise harming, the contact lenses being disinfected and for destroying residual hydrogen peroxide in liquid media used for disinfecting contact lenses.

SUMMARY OF THE INVENTION

New compositions and methods useful to disinfect contact lenses have been discovered. The present invention facilitates the killing of hydrogen peroxide-resistant microorganisms by the action of hydrogen peroxide. Moreover, this is achieved substantially without detriment to the contact lens being disinfected. Further, the residual hydrogen peroxide remaining after the disinfecting takes place is effectively and conveniently destroyed, thus allowing the lens to be safely and comfortably worn.

In one broad aspect, the present invention is directed to compositions which comprise an effective amount of a cellulose and/or chitin decomposing enzyme component, hereinafter referred to as CDEC, for example, lysozyme, and an effective amount of a hydrogen peroxide destroying component, hereinafter referred to as HPDC. Such compositions are structured so that the CDEC is released in a liquid medium before the HPDC is released in the liquid medium. The CDEC is preferably present in an amount effective to render acanthamoeba cysts present in the liquid medium more susceptible to being killed by hydrogen peroxide in the liquid medium than by hydrogen peroxide in a substantially identical liquid medium in the absence of the CDEC. The HPDC is preferably present in an amount effective to destroy all the hydrogen peroxide contained in the liquid medium. Methods for disinfecting contact lenses are also provided in which a contact lens is contacted with a liquid medium containing an effective contact lens disinfecting amount of hydrogen peroxide in the presence of a composition, as described herein.

The present invention preferably allows the CDEC/HPDC-containing composition to be initially contacted with the hydrogen peroxide-containing liquid medium, hereinafter referred to as HPLM, at the same time the contact lens to be disinfected is initially contacted with the liquid medium. For example, the present compositions and the contact lens to be disinfected can be added to the HPLM at substantially the same time. This feature greatly reduces the amount of user time and care required to effectively disinfect his/her lens and destroy the residual hydrogen peroxide. Better user compliance and a greater degree of user eye safety is provided. The present invention preferably includes a delayed release feature so that the contact lens is effectively disinfected, even from hydrogen peroxide-resistant microorganisms, by the action of hydrogen peroxide prior to the release of the HPDC.

In one embodiment, the release of the HPDC is delayed sufficiently long, preferably at least about 1 hour and more preferably at least about 2 hours, to allow relatively low concentrations of CDEC to facilitate the killing of the hydrogen peroxide-resistant microorganisms. Such relatively reduced concentrations of CDEC have the advantage of being less likely to form proteinaceous deposits on the contact lens being treated.

The present compositions may include an effective amount of a cleaning enzyme component to remove deposit material, for example, to clean, the contact lens. In this embodiment, a higher concentration of CDEC may be employed to provide for enhancing the killing effect of hydrogen peroxide. Thus, even if the CDEC forms deposits on the contact lens during the disinfection processing, the cleaning enzyme component is present in an amount effective to remove this deposit material as well as other deposit material from the contact lens. Preferably, the CDEC is released into the liquid medium prior to releasing the cleaning enzyme component.

DETAILED DESCRIPTION OF THE INVENTION

The present invention is of value where hydrogen peroxide is used to disinfect all types of lenses, e.g., contact lenses, which are benefitted by periodical disinfecting. Such lenses, e.g., conventional hard contact lenses and soft contact lenses, may be made of any suitable material or combination of materials and may have any suitable configuration not substantially deleteriously affected by hydrogen peroxide, the present compositions or the present methods.

The present invention is particularly useful for disinfecting a contact lens contaminated with hydrogen peroxide-resistant microorganisms and for destroying residual hydrogen peroxide in a HPLM which has been used to disinfect the contact lens.

The liquid medium used to disinfect a contact lens in the present invention includes a disinfecting amount of hydrogen peroxide. Preferably, a disinfecting amount of hydrogen peroxide means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Relatively mild aqueous hydrogen peroxide solutions, preferably containing about 0.5% to about 6% of hydrogen peroxide (w/v), are known to be effective disinfecting solutions for contact lenses. These solutions are effective at killing bacteria, fungi and yeast which may be found on contact lenses. Moreover, the present invention facilitates the killing of certain hydrogen peroxide-resistant microorganisms, for example, acanthamoeba cysts, which may contaminate contact lenses. However, once a contact lens has been disinfected, the residual hydrogen peroxide, e.g., on the lens, should be destroyed so that the lens may be safely and comfortably worn on the eye. If this residual hydrogen peroxide is not destroyed before the lens is worn, irritation to the eye or wearing discomfort may occur.

Thus, the present compositions, which are preferably initially contacted with the HPLM at substantially the same time as the contact lens to be disinfected, allow for effective lens disinfection, even when the contact lens is contaminated by hydrogen peroxide-resistant microorganisms, and, in addition, effectively destroy the residual hydrogen peroxide remaining in the HPLM so that the disinfected lens can be removed from the liquid medium and placed directly into the eye for safe and comfortable wear. The present composition is preferably present in the solid form, for example, as a tablet, pill and the like. The composition may be present in the form of at least one item, e.g., tablet, which includes a core layer, a coating layer and an outer layer. The coating layer includes a delayed release component and preferably substantially surrounds the core layer, which includes the HPDC. The CDEC is preferably located in the outer layer.

Any suitable CDEC may be employed provided that it is effective to facilitate or enhance the killing action of hydrogen peroxide against hydrogen peroxide-resistant microorganisms, preferably acanthamoeba cysts. Without wishing to limit the invention to any particular theory of operation, it is believed that the CDEC attacks, and/or decomposes and/or otherwise compromises the protective cell wall of the hydrogen peroxide-resistant microorganisms, thereby allowing the hydrogen peroxide in the HPLM to effectively contact and kill the microorganism. The CDEC is chosen and used so as to have no undue detrimental effect on the disinfecting action of hydrogen peroxide, on the lens being disinfected or on the wearer of the contact lens. Examples of useful CDECs include lysozyme, isolysozyme, cellulase, and the like and mixtures thereof. The specific amount of CDEC employed in the present composition depends on many factors, for example, on the specific CDEC being employed, on the specific hydrogen peroxide-resistant microorganisms to be killed and on the contact lens being disinfected.

In use, the CDEC may be present in an amount in the range of about 0.00% or less to about 1% or more (w/v) of the liquid medium employed in disinfecting the contact lens. The presence of the CDEC in the HPLM is preferably effective to result in the killing of acanthamoeba cysts at a rate at least about 2, and more preferably at least about 5 or about 10, times as great relative to a substantially identical HPLM without the CDEC. Care should be taken to avoid using excessive amounts of CDEC. Such excessive amounts of CDEC are wasteful, do not provide any additional microorganism-killing benefits, and can result in heavy soiling and/or other damage to the contact lens being treated.

In certain instances, the CDEC employed can be a component which forms proteinaceous deposit material on the contact lens. A particularly useful example of such a CDEC is lysozyme, which is a primary tear protein.

In order to avoid this deposit formation problem, the concentration of the CDEC may be reduced sufficiently to minimize the formation of deposits derived from the CDEC on the contact lens. Such reduced or non-deposit forming concentrations of the CDEC are at least somewhat effective in facilitating the killing of hydrogen peroxide-resistant microorganisms.

In the event a reduced concentration of CDEC is to be employed, it is often necessary to provide a relatively long period of time for the hydrogen peroxide to contact the lens prior to the HPDC being released in the liquid medium. In a particularly useful embodiment, the CDEC is released in the liquid medium more than 30 minutes prior to the time the HPDC is released in the liquid medium. More preferably, this time is at least about one hour and still more preferably at least about two hours. Such times are useful to allow the CDEC, for example, the reduced concentration of CDEC, to effectively facilitate the killing of the hydrogen peroxide-resistant microorganisms by the action of hydrogen peroxide.

The composition employed in the present invention ray include a cleaning enzyme component in an amount effective to remove the deposit material, for example, the proteinaceous deposit material, that may be formed, for example, from the CDEC, on the contact lens. The cleaning enzyme component is preferably situated in the compositions separate and apart from the CDEC. For example, in the layered composition described previously, the cleaning enzyme component may be included with the HPDC in the core or as a coating directly adjacent the core. In this embodiment, the CDEC is released in the liquid medium, for example, substantially immediately after the composition is initially contacted with the liquid medium, to facilitate the killing of hydrogen peroxide-resistant microorganisms by the hydrogen peroxide in the liquid medium. After a period of time, during which the lens is preferably disinfected, the cleaning enzyme component is released in the liquid medium. Such cleaning enzyme component effectively removes the deposit material originally present on the contact lens and/or the deposit material formed from the CDEC previously released in the liquid medium.

In either case described above, hydrogen peroxide-resistant-microorganisms, such as acanthamoeba cysts, are effectively killed, and the contact lens is effectively disinfected without any significant or undue detrimental effect on the lens, for example, without any soiling of the contact lens by the CDEC.

Any suitable HPDC may be included in the present compositions. Such HPDCs should effectively destroy the residual hydrogen peroxide and have no undue detrimental effect on the disinfected lens or on the eye into which the disinfected lens is placed. Among the useful HPDCs are hydrogen peroxide reducing agents, peroxidases (meaning to include therein catalase) and mixtures thereof.

Examples of the hydrogen peroxide reducing agents which are useful in the present invention are alkali metal in particular sodium, thiosulfates; thiourea; alkali metal, in particular sodium, sulfites; thioglycerol; N-acetylcysteine alkali metal, in particular sodium, formiates; ascorbic acid; isoascorbic acid; glyoxy lic acid; mixtures thereof and the like. A particularly useful peroxidase is catalase. The peroxidases, and especially catalase, are very beneficial in the present invention since such HPDCs are effective to substantially eliminate hydrogen peroxide from a liquid medium in a reasonable period of time, e.g., on the order of about 5 minutes to about 12 hours, preferably about 1 hour to about 5 hours, after the HPDC is initially released into the HPLM.

The amount of HPDC employed is preferably sufficient to destroy all the hydrogen peroxide present in the HPLM into which the HPDC is placed. Excess HPDC may be employed. For example, an excess of HPDC of up to about 40% or more of that amount of HPDC required to destroy all the hydrogen peroxide present in the HPLM may be employed. Larger excesses of HPDC are to be avoided since the HPDC itself may cause problems with the disinfected contact lens and/or the ability to safely and comfortably wear such disinfected contact lens. When catalase is employed as a HPDC, it is preferably present in an amount of about 100 to about 250, more preferably about 150 to about 200, units of catalase activity/percent (w/v) of hydrogen peroxide in the HPLM/ml of HPLM. For example, an especially useful amount of catalase for use in an aqueous solution containing about 3% (w/v) hydrogen peroxide is about 520 units of catalase activity/ml of solution.

The HPDC may be combined with one or more other components, e.g., in the core of a layered tablet. Such other components may include, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here. An illustrative HPDC-containing core tablet may have the following composition:

|  | Wt % |
| --- | --- |
| HPDC | 1–30 |
| Filler | 15–90 |
| Tonicity Agent | 1–30 |
| Buffer | 2–50 |
| Lubricating Agent | 0–30 |

Useful tonicity agents include, but are not limited to, sodium chloride, potassium chloride, mannitol, dextrose, glycerin, propylene glycol and mixtures thereof.

Useful contact lens conditioning/wetting agents include, but are not limited to, polyvinyl alcohol, polyoxamers, polyvinylpyrrolidone, hydroxypropylmethyl cellulose and mixtures thereof. Certain of the present coating components may provide one or more other useful functions after being dissolved in the HPLM.

Useful buffering agents include, but not limited to, acetate buffers, citrate buffers, phosphate buffers and borate buffers. Acids and bases may be used to adjust the pH of the present compositions as needed.

Useful lubricating agents include, but are not limited to, polyalkylene glycols, such as polyethylene glycols, preferably having molecular weights in the range of about 500 to about 10,000. Other materials conventionally used as lubricants in ophthalmically acceptable tablets may be employed in the present invention.

The inclusion of one or more of such other components in the present compositions may be important to facilitate the functioning of such compositions and the present methods.

For example, it may be desirable to maintain the pH and/or osmolality of the liquid aqueous medium within certain ranges, for example, to obtain preferred enzyme activities, delayed release component solubility and/or physiological acceptance. One or more of such other components may be included in the present coated or layered item or items. Also, such other component or components may be included in the present compositions separate and apart from the present coated or layered item or items.

In a particularly useful embodiment, the HPDC is combined with the cleaning enzyme component effective to remove debris, for example, protein-based debris, from a contact lens. Among the types of debris that form on contact lenses during normal use are protein-based debris, mucin-based debris, lipid-based debris and carbohydrate-based debris. One or more types of debris may be present on a single contact lens.

The cleaning enzyme component employed may be selected from enzymes, for example, peroxide-active enzymes, which are conventionally employed in the enzymatic cleaning of contact lenses. For example, many of the cleaning enzymes disclosed in Huth et. al. U.S. Pat. Re No. 32,672 and Karageozian et al U.S. Pat. No. 3,910,296 are useful in the present invention. These patents are incorporated in their entirety by reference herein. Among the useful cleaning enzymes are those selected from proteolytic enzymes, lipases, carbohydrate-active (carbolytic) enzymes and mixtures thereof.

Preferred proteolytic enzymes are those which are substantially free of sulfhydryl groups or disulfide bonds, whose presence may react with the active oxygen in the HPLM to the detriment of the activity of the enzyme. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II alkaline Proteases." Biotechnology and Bioengineering, Vol. XII, pp 213–249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two sub-classes, subtilisin A and subtilisin B. In the subtilism A grouping are enzymes derived from such species are *B. subtilis*, *B. licheniformis* and *B. pumilis*. Organisms in this sub-class produce little or no neutral protease or amylase. The subtilisin B sub-class is made up of enzymes from such organisms as *B. subtilis*, *B. subtilis var. amylosacchariticus*, *B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of cleaning enzyme component is to be used in the practice of this invention. Such amount will be that amount which effects removal in a reasonable time (for example overnight) of substantially all of at least one type of debris, for example, proteinaceous deposits, from a lens due to normal wear. This standard is stated with reference to contact lens wearers with a history of normal pattern of debris accretion, not the very small group who may at one time or another have a significantly increased rate of debris accretion such that cleaning is recommended every day, or every two or three days.

The amount of cleaning enzyme component required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Although multi-layered (including core and coating layering) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Items which release their ingredients in a sequential, time delayed manner are well known and can be produced using conventional technology. Therefore, a detailed description of such items and such production technology is not presented here. However, such items are designed to allow the CDEC a period of time, preferably a period of time sufficient to disinfect the lens in the HPLM, before releasing the HPDC in the liquid medium. In other words, such items or compositions are designed so that sufficient time elapses between initial contact with the liquid medium and release of the HPDC to allow the CDEC to perform its function. Such sufficient time is preferably more than 30 minutes, more preferably more than about 1 hour and still more preferably more than about 2 hours. Such period of time is preferably less than about 6 hours.

In one useful embodiment, a direct compression is made of the core tablet formulation using conventional tableting equipment. A liquid, for example, solution, containing the delayed release component is applied, e.g., sprayed, onto the core tablet using conventional coating equipment, such as film coating pans or fluid beds. Coating pan equipment is available from Driam of West Germany, Thomas Engineering, vector Corporation, and Key Industries in the U.S. Fluid bed equipment is available from Glatt Air Techniques, vector Corporation, and Aeromatic, as well as other companies. Using appropriate coating parameters, which are dependent on, for example, the specific composition of the delayed release component-containing solution, the equipment used and core tablet size, an appropriate amount of delayed release component is applied to the core table that allows the desired delay release time. The CDEC is then applied to the outer surface of the delayed release component, for example, by spraying, dipping, other coating processing, etc.

Any suitable delayed release component or combination of delayed release components may be employed, provided that such component or components function as described herein and have no substantial detrimental effect on the CDEC, on the HPDC (and on the cleaning enzyme component, if any), on the lens being treated and on the mammal, for example, human, wearing the treated lens. The delayed release component is preferably at least partially, more preferably completely, water soluble. The delayed release component preferably comprises a major amount of at least one polymeric material. Examples of useful delayed release components include, but are not limited to, soluble cellulose ethers such as methylcellulose, methylhydroxypropylcellulose, methylhydroxyethylcellulose, hydroxypropylcellulose, hydroxyethylcellulose and sodium carboxymethylcelluloses; cellulose esters such as cellulose acetate phthalate and hydroxypropylmethyl-cellulose phthalate; polymers derived from at least one of acrylic acid, acrylic acid esters, methacrylic acid and methacrylic acid esters such as methacrylic acid-methyl methacrylate copolymer (for example that sold by Rohm Pharma under the trademark Eudragit L 100) and methacrylic acid-ethyl acrylate copolymers (for example that sold by Rohm Pharma under the trademark Eudragit L 30D); polymers derived from methyl vinyl ether and maleic acid anhydride; polyvinylpyrrolidone; polyvinyl alcohols and the like and mixtures thereof.

The present methods of disinfecting a lens, preferably a contact lens, include contacting the lens to be disinfected with a HPLM at effective lens disinfecting conditions. The HPLM is contacted with a composition which includes the CDEC, the HPDC and a delayed release component, such as described herein. Using this method, the lens is disinfected and the residual hydrogen peroxide in the HPLM is effectively destroyed. Thus, after thee HPDC has been released into the HPLM and acts to effectively destroy the residual HPDC, the lens can be safely and comfortably taken directly from the liquid medium in which it was disinfected.

In a particularly useful embodiment, the contact lens to be disinfected is placed into the HPLM at substantially the same time as in the CDEC/HPDC-containing composition. After a predetermined period of time, during which the contact lens is disinfected, the HPDC is released into the HPLM and effectively destroys the residual hydrogen peroxide.

In the event that a cleaning enzyme component is present in the composition, the contact lens in the liquid medium is also effectively cleaned of at least one type of deposit material, for example, any protein-based debris. This cleaning action preferably occurs after the lens is disinfected, with the cleaning enzyme component being released in the HPLM after the CDEC is so released and before or at the same time the HPDC is released in the HPLM or thereafter.

It is preferred that substantially all of the residual hydrogen peroxide in the HPLM be destroyed in less than about 12 hours, more preferably in less than about 6 hours and still more preferably in less than about 4 hours, after the HPDC is initially released in the HPLM.

The disinfecting contacting preferably occurs at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. This contacting preferably occurs for a time to substantially completely disinfect the lens being treated. Such contacting times can be in the range of about 30 minutes or more than 30 minutes to about 12 hours or more.

The following non-limiting examples illustrate certain aspects of the present invention.

EXAMPLE 1

A three layer tablet, having a core tablet surrounded by a delayed release layer coated by an outer layer containing lysozyme is prepared. The three layer tablet contains about 5 to 10 mg of lysozyme. The core tablet and delayed release layer had the following compositions:

| CORE TABLET | |
|---|---|
| Crystalline catalase[1] | 1 mg |
| Sodium chloride | 89 mg |
| Dibasic sodium phosphate (anhydrous) | 12.5 mg |
| Monobasic sodium phosphate monohydrate | 1 mg |
| Polyethylene glycol (molecular weight of about 3350) | 1 mg |
| Hydroxypropylmethyl cellulose | 10 to 20 mg |
| COATING LAYER | |
| Hydroxypropylmethyl cellulose | 6 to 10 mg |

[1]The amount of catalase added is determined by an assay of the batch of product to be used. The core tablets, which are produced by direct compression, each contain at least 3000 units of catalase activity, but no more than 7280 units of catalase activity.

EXAMPLE 2

A three layer tablet in accordance with Example 1 is used to disinfect a conventional soft contact lens as follows. 10 ml of a 3% (w/v) aqueous solution of hydrogen peroxide is provided at room temperature. The contact lens to be disinfected, which is contaminated with acanthamoeba cysts, and the three layer tablet are placed in the solution at the same time. For approximately 2 to 2.5 hours, the solution remains substantially quiet, i.e., substantially no bubbling (gas evolution) takes place. For the next approximately two hours, the solution bubbles. After this period of time, the solution becomes and remains quiet. Five hours after the contact lens is first introduced into the solution, it is removed from the solution, rinsed with saline solution and placed into the wearer's eye. It is found that after four hours, the contact lens is effectively disinfected. Also, the lens wearer experiences no discomfort or eye irritation from wearing the disinfected contact lens. The bubbling of the solution provides a indication that hydrogen peroxide destruction is occurring. An indication that the peroxide destruction is complete is provided when the bubbling stops.

EXAMPLE 3

A three layer tablet is prepared as in Example 1 except that sufficient subtilisin A is included in the core tablet to provide the core tablet with 10 ppm (by weight) of this enzyme.

This enzyme containing tablet is used to disinfect and clean a protein-based debris laden soft contact lens which is contaminated with acanthamoeba cysts as follows. 10 ml of a 3% (w/v) aqueous solution of hydrogen peroxide is provided at room temperature. The contact lens to be disinfected and cleaned and the cleaning enzyme-containing three layer tablet are placed in the solution at the same time. For approximately 2 to 2.5 hours the solution remains substantially quiet. For the next approximately two hours, the solution bubbles. After this period of time, the solution becomes and remains quiet. 10 hours after the contact lens is first introduced into the solution, it is removed from the solution, rinsed with saline solution and placed into the wearer's eye. It is found that after 10 hours, the contact lens is effectively disinfected and cleaned of protein-based debris. The lens wearer experiences no discomfort or eye irritation from wearing the disinfected and cleaned contact lens.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
contacting a contact lens with a liquid medium initially containing an effective contact lens disinfecting amount of hydrogen peroxide in the presence of a composition comprising a cellulose decomposing enzyme component, a cleaning enzyme component and a hydrogen peroxide destroying component, said composition being structured so that said cellulose decomposing enzyme component is released in said liquid medium before said hydrogen peroxide destroying component is released in said liquid medium and said cleaning enzyme component is released in said liquid medium after said contact lens is disinfected, said cellulose decomposing enzyme component being present in an amount effective to render acanthamoeba cysts present in said liquid medium more susceptible to being killed by hydrogen peroxide in said liquid medium than by hydrogen peroxide in a substantially identical liquid medium in the absence of said cellulose decomposing enzyme component, said cleaning enzyme component is present in an amount effective to remove the protein deposits on said contact lens prior to said contacting and the Drotein deposits formed on said contact lens during said contacting from said cellulose decomposing enzyme component from said contact lens, and said hydrogen peroxide destroying component is present in an amount effective to destroy all the hydrogen peroxide contained in said liquid medium, said contacting being effective to disinfect said contact lens, to form protein deposits from said cellulose decomposing enzyme on said contact lens and to remove protein deposits present on said contact lens prior to said contacting and protein deposits formed on said contact lens during said contacting from said cellulose decomposing enzyme component from said contact lens.

2. The method of claim 1 wherein prior to said contacting said contact lens is contaminated with acanthamoeba cysts.

3. The method of claim 1 wherein said cellulose decomposing enzyme component includes lysozyme.

4. The method of claim 1 wherein said cleaning enzyme component is released in said liquid medium after said cellulose decomposing enzyme component is released in said liquid medium and at substantially the same time said hydrogen peroxide destroying component is released in said liquid medium.

5. A composition comprising a cellulose decomposing enzyme component, a hydrogen peroxide destroying component, an amount of a cleaning enzyme component effective to remove the protein deposits from a contact lens present in a liquid medium in which said cleaning enzyme component is released, the protein deposits including the protein deposits present on said contact lens prior to said contact lens being present in the liquid medium and the protein deposits formed on said contact lens from said cellulose decomposing enzyme component, and a delayed release component, said composition being a solid and structured so that said cellulose decomposing enzyme component is released in said liquid medium before said hydrogen peroxide destroying component is released in said liquid medium and said cleaning enzyme component is released in said liquid medium at substantially the same time said hydrogen peroxide destroying component is released in said liquid medium, said cellulose decomposing enzyme component being present in an amount effective to render acanthamoeba cysts present in said liquid medium more susceptible to being killed by hydrogen peroxide in said liquid medium than by hydrogen peroxide in a substantially identical liquid medium in the absence of said cellulose decomposing enzyme component and to form protein deposits from said cellulose decomposing enzyme component in the presence of hydrogen peroxide on said contact lens, said hydrogen peroxide destroying component being present in an amount effective to destroy all the hydrogen peroxide contained in said liquid medium, and said delayed release component being present in an amount effective to delay the release in said liquid medium of said hydrogen peroxide destroying component for a sufficient time to allow a contact lens introduced into said liquid medium at substantially the same time as said composition to be disinfected.

6. The composition of claim 5 which is structured so that said cellulose decomposing enzyme component is released in said liquid medium at least about one hour before said hydrogen peroxide destroying component is released in gaid liquid medium.

7. The composition of claim 5 which is structured so that said cellulose decomposing enzyme component is released in said liquid medium at least about two hours before said hydrogen peroxide destroying component is released in said liquid medium.

8. The method of claim 1 wherein said composition is structured so that said cellulose decomposing enzyme component is released in said liquid medium at least about two hours before said hydrogen peroxide destroying component is released in said liquid medium.

9. The method of claim 1 wherein said composition includes a delayed release component in an amount effective to delay the release in said liquid medium of said hydrogen peroxide destroying component for a sufficient time to allow a contact lens introduced into said liquid medium at substantially the same time as said composition to be disinfected.

10. The composition of claim 5 wherein said cellulose decomposing enzyme component includes lysozyme.

11. The composition of claim 5 which is in the form of a tablet or a pill.

12. The composition of claim 5 wherein said cellulose decomposing enzyme component is situated so as to be released in said liquid medium substantially immediately after said composition is initially contacted with said liquid medium, and said delayed release component is present in an amount effective to delay the release in said liquid medium of said hydrogen peroxide destroying component for more than 30 minutes after said composition is initially contacted with said liquid medium.

13. The composition of claim 12 wherein said delayed release component is present in a coating substantially surrounding said hydrogen peroxide destroying component.

14. The composition of claim 12 wherein said delayed release component is selected from the group consisting of cellulose ethers, cellulose esters, polymers derived from at least one of acrylic acid, acrylic acid esters, methacrylic acid and methacrylic acid esters, polymers derived from methyl vinyl ether and maleic acid anhydride, polyvinylpyrrolidone, polyvinyl alcohols and mixtures thereof.

15. The composition of claim 5 wherein said hydrogen peroxide destroying component is selected from the group consisting of reducing agents capable of chemically reducing hydrogen peroxide in said liquid medium, catalase and mixtures thereof.

* * * * *

UNITED STATES PATENT AND TRADEMARK OFFICE
CERTIFICATE OF CORRECTION

PATENT NO.       : 6,338,847 B1                                               Page 1 of 1
DATED            : January 15, 2002
INVENTOR(S)      : Thomas It is certified that error appears in the above-identified patent and that said Letters Patent is hereby corrected as shown below:

<u>Column 4,</u>
Line 57, "0.00%" should be -- 0.001% --.

<u>Column 5,</u>
Line 25, "ray" should be -- may --.
Line 65, "glyoxy lic" should be -- glyoxylic --.

<u>Column 8,</u>
Lines 54 and 56, "vector" should be -- Vector --.

<u>Column 11,</u>
Line 41, "Drotein" should be -- protein --.

<u>Column 12,</u>
Line 38, "gaid" should be -- said --.

Signed and Sealed this

Tenth Day of June, 2003

JAMES E. ROGAN
*Director of the United States Patent and Trademark Office*